(12) United States Patent
Bhardwaj et al.

(10) Patent No.: US 6,602,433 B1
(45) Date of Patent: Aug. 5, 2003

(54) GAS DELIVERY SYSTEM

(75) Inventors: Jyoti Kiron Bhardwaj, Bristol (GB); Nicholas Shepherd, Cardiff (GB); Leslie Michael Lea, Oxfordshire (GB)

(73) Assignee: Surface Technology Systems PLC, Gwent (GB)

(*) Notice: Subject to any disclaimer, the term of this patent is extended or adjusted under 35 U.S.C. 154(b) by 0 days.

(21) Appl. No.: 09/674,658
(22) PCT Filed: Mar. 6, 2000
(86) PCT No.: PCT/GB00/00789
§ 371 (c)(1), (2), (4) Date: Dec. 18, 2000
(87) PCT Pub. No.: WO00/52740
PCT Pub. Date: Sep. 8, 2000

(30) Foreign Application Priority Data

Mar. 4, 1999 (GB) ............................................. 9904925

(51) Int. Cl.$^7$ ................................................. B44C 1/22
(52) U.S. Cl. ............................. 216/37; 216/58; 216/73; 216/67; 156/345.29
(58) Field of Search ............................. 216/37, 58, 73, 216/67; 156/345.29

(56) References Cited

U.S. PATENT DOCUMENTS

| 4,160,690 A | * | 7/1979 | Shibagaki et al. | ........... 156/643 |
| 6,033,969 A | * | 3/2000 | Tsai et al. | .................. 438/425 |

* cited by examiner

*Primary Examiner*—William A. Powell
(74) *Attorney, Agent, or Firm*—Volentine Francos, PLLC

(57) ABSTRACT

A substrate is treated by supplying an etchant and/or deposition gas into a chamber in which the substrate is situated. In order to avoid the problems associated with transportation of toxic gases, the gases required for such processes are delivered directly from a gas generation and delivery system positioned locally to the chamber.

13 Claims, 1 Drawing Sheet

GAS DELIVERY SYSTEM

Figure 1:
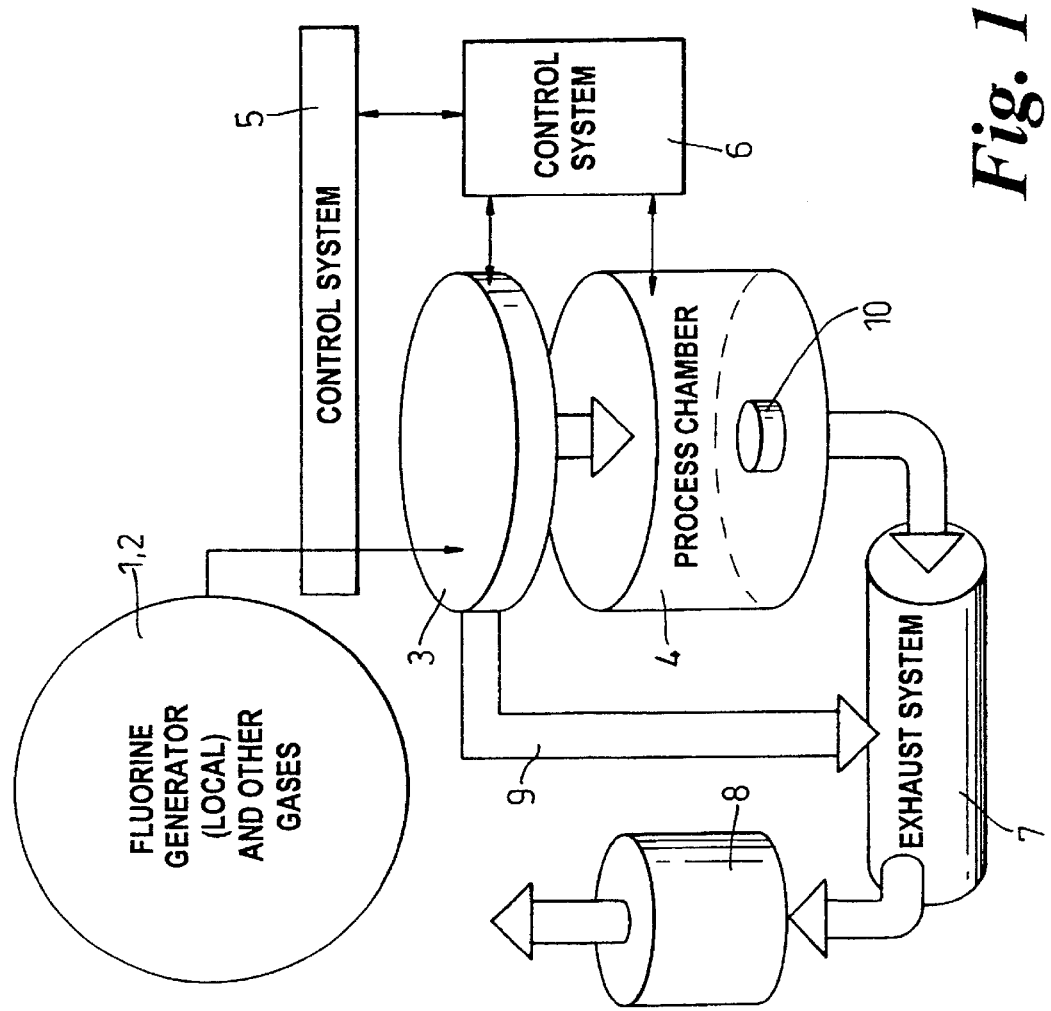

This invention relates to a gas delivery system, particularly, although not exclusively, one for use in dry processing apparatus, for example one in which a switched etch/deposition cycle or continuous process is used on a semiconductor wafer or the like.

Continuous plasma processes as well as switched etch/deposition processes use sulphur hexafluoride as the standard etch chemistry. The industry demands for higher etch rate processes have led to the investigation of alternative process etch gases which allow an increase in the density of active species in the process chamber resulting in improved process rates.

Several different chemistries are known to be likely candidates to enhance the process rate. All suffer from increased cost, greater health and safety risks and poor commercial availability. These factors combine to make the economics of implementing these chemistries extreme and/or the installation too hazardous. Latterly, a number of molten electrolyte gas generators have been reported and are just being made commercially available. Generation of gases by this means includes fluorine, nitrogen trifluoride and chlorotrifluoride. An example is a fluorine gas generator cell as described in U.S. Pat. No. 5,688,384. The generators are able to generate the process gases to high purity and at a reasonable cost and risk. The gas generators contain a solid when cold and this allows for safe transportation and storage of the units.

The incorporation of these gas generators into a gas delivery system local to the process chamber allows a novel capability to introduce different processes gases into a variety of process schedules to achieve a process advantage. There are many novel aspects to the application of these gas generators to a dry processing environment in terms of system design, gas delivery control, system transportation, ease of installation and process advantages.

Thus, according to a first aspect of the present invention there is provided an apparatus for treating a substrate, the apparatus comprising a chamber, a support for a substrate and a delivery system for delivering an etchant and/or a deposition gas into the chamber, wherein the delivery system is positioned locally to the chamber.

"Locally" (or point of use) means that the delivery system is located near to a process chamber or a number of chambers or number of systems near to one another, so that the gases created can be delivered directly to the chamber or system for immediate use rather than being created off-site and transported in a suitable container for subsequent introduction into the apparatus.

The delivery system will preferably include a molten electrolyte gas generator

According to a second aspect of the present invention, there is provided a method of treating a substrate comprising providing an etchant and/or deposition gas to a chamber in which the substrate is situated, wherein the gas is delivered from a delivery system positioned locally to the chamber.

According to a third aspect of the present invention, there is provided a method of treating a substrate comprising cyclically performing the following steps:
a) etching the substrate with a gas;
b) depositing a passivation layer on the surface of an etched feature; and
c) selectively removing the passivation layer from the base of the etched feature,
wherein the etchant gas comprises fluorine, nitrogen trifluoride or chlorotrifluoride or mixtures thereof generated locally.

If desired such gases can be mixed with $SF_6$ or other known etchant gases.

Ideally, in the methods of the invention as defined above, the gases are supplied from a delivery system including a molten electrolyte gas generator.

Safety issues compared to the conventional cylinder delivery:
1. The generators operate at or near atmospheric pressure eliminating the need for high pressure regulators on the system.
2. There is no potentially hazardous gas in the system until the user demands production eliminating hazardous storage problems. The risks to operators are significantly reduced.
3. At room temperature the gas generators have a solid constitution eliminating the risks of transporting the hazardous gas on site or to the working location.
4. The local delivery on demand eliminates long gas lines from a central store on the installation and the associated risks of hazardous gases in these pipes.

Reduced cost of installations of the gas generators compared to conventional cylinder delivery.
1. The local delivery system eliminates the expense to add additional long gas lines from a central store on the installation to the processing environment.
2. The production and quality of the process gas from the generator is typically comparable to that produced by the high pressure cylinders.
3. The close proximity to the process equipment minimises the safety precautions needed to protect the operator during any maintenance operations.

Features of this novel use and design of the gas generators may be:
1. A totally dry method of heating the electrolyte instead of the normal hot water bath.
2. The gas generators produce a gas at both the anode and the cathode of the electrolytic cell. The two gases are potentially extremely reactive but are separated by the design of the system to avoid any possible recombination.
3. The gas generators are only designed to be operated at or near atmospheric pressure. The design of the gas line to the process chamber incorporates a novel control system such that the generator does not see the low pressure (vacuum) at the process chamber. This is an important design feature of the gas generators operation on the overall system.
4. Included in the local delivery system is the ability to polish the generated gas to remove unwanted impurities before passing into the process chamber.

It is envisaged that the invention can be used in our following co-pending applications:
1. Continuous operation dry processing (European Patent Application No. 9909091.3). The gas generator can be used to supply a process gas to etch substrates placed in the process chamber. This may involve the use of a plasma to generate the reactive species or without a plasma where the generated gas reacts spontaneously with the substrate.
2. Alternative gas for the switched plasma process (EP-A-0822584 and EP-A-0822582). The addition of the generated gas allows the replacement or addition to the existing process etch gas used in the switched plasma process. The generated gas e.g. fluorine, nitrogen trifluoride or chlorotrifluoride can be advantageously used to enhance the process etch rate either individually or in combination with the existing sulphur hexafluoride.

3. Alternative gas for the plasma-less switched process (International Patent Application No. PCT/GB99/02368). Where the generated gas spontaneously reacts with the substrate, substitution of the sulphur hexafluoride process gas will also allow the operation of the process without plasma in the process chamber.

In addition, it is envisaged that the invention can be used in the generation of gases for a plasma/plasma-less switched process similar to that in International Patent Application No. PCT/GB99/02368. The ability to generate gases or combine gas mixtures which either require a plasma to produce the reactive species or spontaneously react with the substrate, allows the capability to introduce a process schedule which may only require a plasma for one or other the process steps in the overall process schedule. The invention may be performed in various ways and preferred embodiments thereof will now be described, by way of example, with reference to the accompanying FIG. 1 comprising a diagrammatic illustration of a general gas generation system of this invention.

In the arrangement shown in FIG. 1, one or more precursor gases are passed from one or more suitable supply source(s) 1, 2 to a process chamber 4 where a dry process utilising that gas is to take place. Appropriate valving will include one or more valves provided at 3 for appropriate control and isolation means. Linked control systems 5 and 6 monitor and maintain the required gas supply to either the process chamber 4 or to the bypass line 9.

From the process chamber 4 gases pass to an exhaust system 7, which in turn leads to an abatement tool 8 (which is usually needed). The bypass outlet 9 leads from the reaction chamber 3 to the exhaust system, whereby gases can be switched into the process chamber only when required for processing. This also allows the means for ensuring stable gas composition and flow to be maintained prior to switching into the process chamber. Within the process chamber 4 there is a support 10 for a substrate which is to be treated by the supplied gas(es).

What is claimed is:

1. An apparatus for treating a substrate, the apparatus comprising a chamber, a support for a substrate and a gas generation and delivery system for delivering an etchant gas into the chamber, wherein the gas generation and delivery system is positioned locally to the chamber.

2. An apparatus for treating a substrate, the apparatus comprising a chamber, a support for a substrate and a gas generation and delivery system for delivering an etchant gas into the chamber, wherein the gas generation and delivery system is positioned locally to the chamber, and wherein the gas generation and delivery system includes a molten electrolyte gas generator.

3. A method of treating a substrate comprising providing an etchant gas to a chamber in which the substrate is situated, wherein the gas is delivered from a gas generation and delivery system positioned locally to the chamber.

4. A method of treating a substrate comprising cyclically performing the following steps:
a) etching the substrate with a gas;
b) depositing a passivation layer on the surface of an etched feature; and
c) selectively removing the passivation layer from the base of the etched feature,
wherein the etchant gas comprises fluorine, nitrogen trifluoride or chlorotrifluoride or mixtures thereof generated locally.

5. A method according to claim 4, wherein said etchant gas is mixed with $SF_6$.

6. A method according to claim 4, wherein the gases are supplied from a gas generation and delivery system including a molten electroyte gas generator.

7. A method according to claim 5, wherein the gases are supplied from a gas generation and delivery system including a molten electroyte gas generator.

8. An apparatus for treating a substrate, the apparatus comprising a chamber, a support for a substrate and a gas generation and delivery system for delivering a deposition gas into the chamber, wherein the gas generation and delivery system is positioned locally to the chamber.

9. An apparatus for treating a substrate, the apparatus comprising a chamber, a support for a substrate and a gas generation and delivery system for delivering a deposition gas into the chamber, wherein the gas generation and delivery system is positioned locally to the chamber, and wherein the gas generation and delivery system includes a molten electrolyte gas generator.

10. A method of treating a substrate comprising providing a deposition gas to a chamber in which the substrate is situated, wherein the gas is delivered from a gas generation and delivery system positioned locally to the chamber.

11. An apparatus for treating a substrate, the apparatus comprising a chamber, a support for a substrate and a gas generation and delivery system for delivering an etchant and a deposition gas into the chamber, wherein the gas generation and delivery system is positioned locally to the chamber.

12. An apparatus for treating a substrate, the apparatus comprising a chamber, a support for a substrate and a gas generation and delivery system for delivering an etchant and a deposition gas into the chamber, wherein the gas generation and delivery system is positioned locally to the chamber, and wherein the gas generation and delivery system includes a molten electrolyte gas generator.

13. A method of treating a substrate comprising providing an etchant and a deposition gas to a chamber in which the substrate is situated, wherein the gas is delivered from a gas generation and delivery system positioned locally to the chamber.

* * * * *